(12) United States Patent
Damron (10) Patent No.: US 10,912,548 B2
(45) Date of Patent: Feb. 9, 2021

(54) SURGICAL RETRACTOR ADAPTOR DEVICES AND METHODS OF USE THEREOF

(71) Applicant: The Research Foundation for The State University of New York, Syracuse, NY (US)

(72) Inventor: Timothy A. Damron, Syracuse, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 16/225,877

(22) Filed: Dec. 19, 2018

(65) Prior Publication Data

US 2019/0183477 A1    Jun. 20, 2019

Related U.S. Application Data

(60) Provisional application No. 62/607,701, filed on Dec. 19, 2017.

(51) Int. Cl.
*A61B 17/02* (2006.01)
*A61B 90/50* (2016.01)
(Continued)

(52) U.S. Cl.
CPC .......... *A61B 17/0206* (2013.01); *A61B 17/02* (2013.01); *A61B 90/50* (2016.02);
(Continued)

(58) Field of Classification Search
CPC ................ A61B 17/0206; A61B 17/02; A61B 2017/00477; A61B 2017/00858;
(Continued)

(56) References Cited

U.S. PATENT DOCUMENTS 837,996 A * 12/1906 Youngman ............. G09B 15/00
84/466
1,139,627 A * 5/1915 Baltzley .................. D06F 55/00
24/565

(Continued)

*Primary Examiner* — Eduardo C Robert
*Assistant Examiner* — David C Comstock (57) ABSTRACT

One aspect of the invention relates to an adaptor for use in a surgical retractor system including a surgical retractor bar having a longitudinal extent between a first end and a second end and a self-retaining retractor device with arms moveable between spaced and proximate positions. The adaptor includes a first plate coupled to a second plate, optionally by one or more connecting elements. A slot is formed between the first plate and the second plate and is configured to either longitudinally receive either the first end or the second end of the surgical retractor bar or laterally receive a lateral edge of the surgical retractor bar such that the adaptor is positioned along the longitudinal extent between the first end and the second end of the surgical retractor bar during use. One or more retaining elements are located on a first surface of the first plate opposite the slot between the first plate and the second plate. The one or more retaining elements are shaped to engage with at least a portion of the self-retaining retractor device to maintain the position of the self-retaining retractor device with respect to the first surface when a force is applied oblique to the first surface by the self-retaining retractor device.

20 Claims, 5 Drawing Sheets

(51) Int. Cl.
    *A61B 1/32*     (2006.01)
    *A61B 17/00*    (2006.01)
    *A61B 90/30*    (2016.01)
(52) U.S. Cl.
    CPC ............... *A61B 1/32* (2013.01); *A61B 90/30* (2016.02); *A61B 2017/00477* (2013.01); *A61B 2017/00858* (2013.01)
(58) Field of Classification Search
    CPC ........... A61B 90/50; A61B 90/30; A61B 1/32; A61B 17/0212
    USPC ....... 600/201, 203, 210, 213, 215, 217, 219, 600/223, 226, 227, 228, 229, 231, 234
    See application file for complete search history.

(56) References Cited

U.S. PATENT DOCUMENTS

| | | | | |
|---|---|---|---|---|
| 4,467,791 | A * | 8/1984 | Cabrera | A61B 90/50 248/229.16 |
| 6,504,985 | B2 * | 1/2003 | Parker | A61B 17/02 362/559 |
| 9,161,745 | B2 | 10/2015 | Dodson | |
| 9,169,961 | B1 * | 10/2015 | Jiang | F16M 11/12 |
| 2007/0213596 | A1 * | 9/2007 | Hamada | A61B 17/02 600/219 |
| 2011/0082347 | A1 * | 4/2011 | Okoniewski | A61B 17/0218 600/227 |
| 2012/0041268 | A1 * | 2/2012 | Grey | A61B 90/30 600/199 |
| 2014/0323811 | A1 * | 10/2014 | DeSantis | A61B 1/06 600/213 |
| 2017/0312045 | A1 * | 11/2017 | McGuire | A61B 90/30 |

\* cited by examiner

FIG. 1
Retractor bars

SURGICAL RETRACTOR ADAPTOR DEVICES AND METHODS OF USE THEREOF

This application claims the benefit of U.S. Provisional Patent Application Ser. No. 62/607,701, filed Dec. 19, 2017, which is hereby incorporated by reference in its entirety.

FIELD OF THE INVENTION

The present invention relates to an adaptor device for use with surgical retractors and methods of use thereof. More specifically, the present invention relates to an adaptor that enables a self-retaining retractor (Weitlaner or Gelphi) to engage with a manually operated retractor bar (Hohmann) so that the self-retaining retractor can hold the retractor bars apart to maintain tissue separation in a surgical field.

BACKGROUND OF THE INVENTION

A retractor is a surgical instrument which can be used either to actively separate the edges of a surgical incision or wound or to hold back underlying organs and tissues so that tissue and/or organs under the incision may be accessed. While there are many types of retractors used in surgery, they all generally fall into one of two categories: those that are self-retaining (i.e., able to lock into position to maintain retraction of tissue or organs without a manual force being actively applied to the retractor, such as by a person's hand) and those that are not. During surgeries it is preferable to use a self-retaining retractor, such as a Weitlaner or Gelpi retractor (very common retractors used by most surgeons worldwide), whenever possible because doing so eliminates the need for an extra pair of hands, and person in the operating room, to actively hold the retractor or retractors in position and maintain the tissue separation or organ displacement. An extra person increases cost and operating room crowding. The extra hands and person may also interfere with the surgical field and access to the wound.

Figure 1:
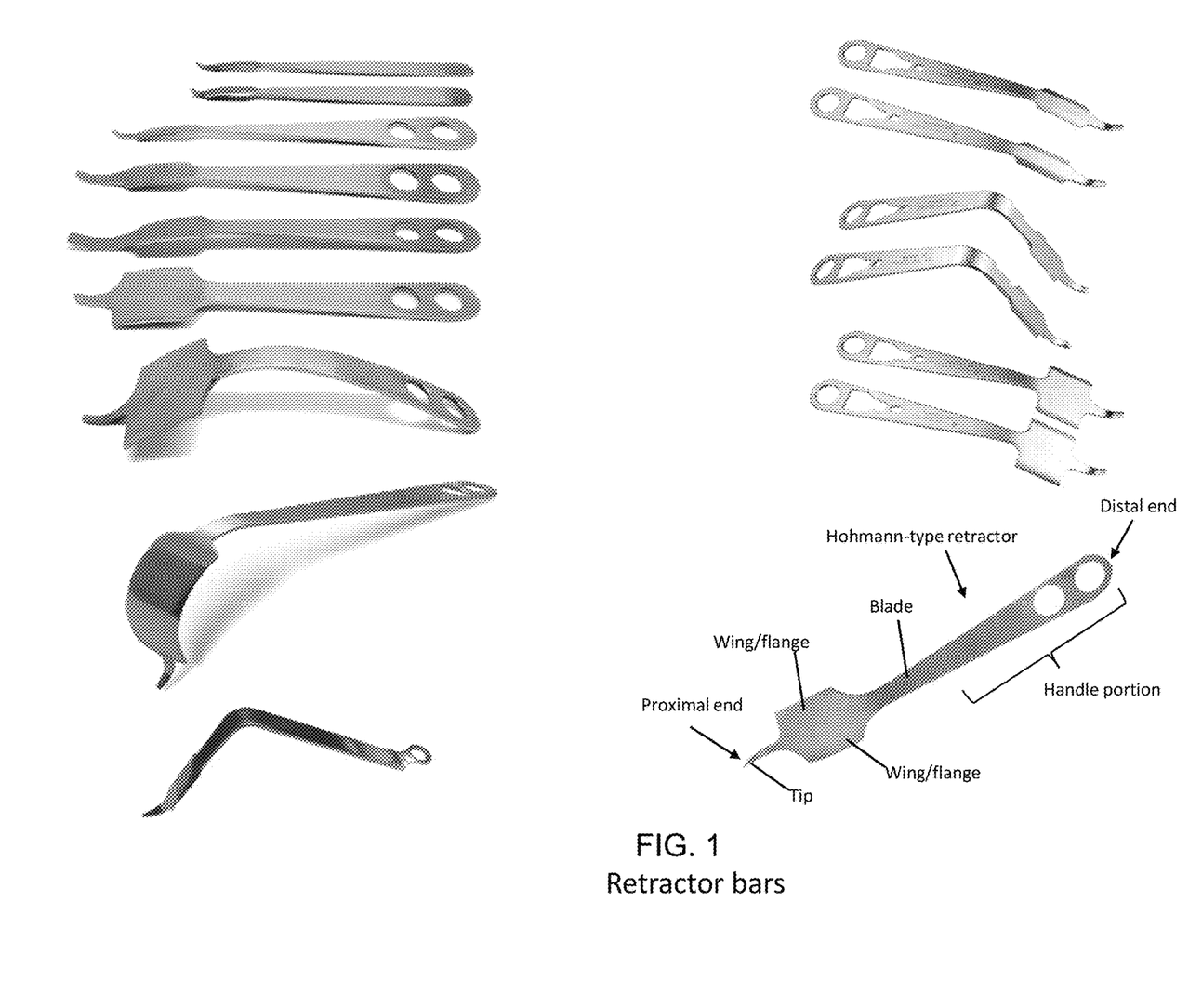
FIG. 1 is an image of various retractor bars that may be utilized with the present invention.
Figure 2:
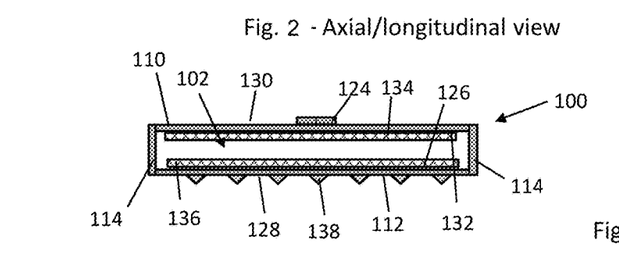
FIG. 2 is a top view of an exemplary adaptor, for use with surgical retractors, of the present invention.
Figure 3:
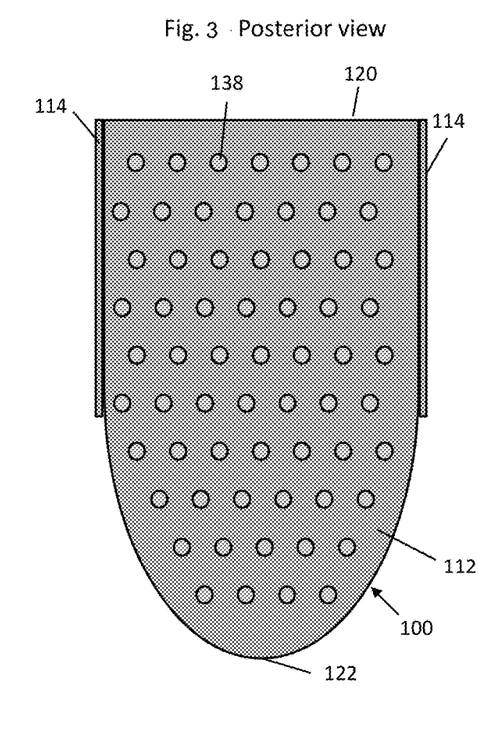
FIG. 3 is a rear view of the exemplary adaptor shown in FIG. 1.
Figure 4:
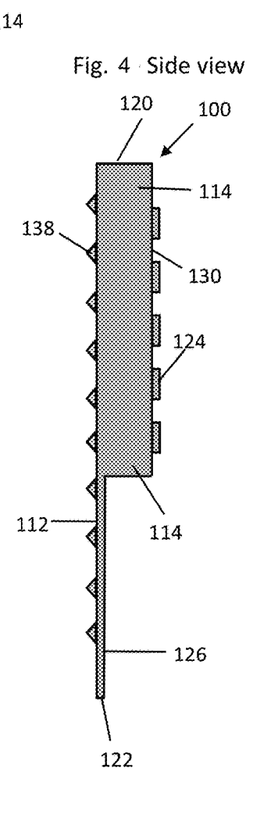
FIG. 4 is a side view of the exemplary adaptor shown in FIG. 1.

There are, however, certain circumstances or retraction tasks for which no self-retaining retractor is available or appropriate. Retractor bars (e.g., Hohmann retractors) are used by orthopedic surgeons for certain tasks and are not self-retaining. One example of their use is in surgeries on the femur where they are used to pull the edges of the surgical incision apart and provide the surgeon unimpeded access to the bone. In order for retractor bars to maintain tissue separation or displacement, an external applied force is necessary; in most cases this external force is applied by a person holding the retractor bars in position Retractor bars come in a wide variety of shapes and sizes, at least several different of which are found in the tool chests of most orthopedic surgeons (FIG. 1 shows various retractor bars). Retractor bars consist of a long straight, slightly curved or bent blade (generally with a mostly planar cross-section—front and back sides parallel) made of a stiff and strong material, such as metal (e.g., stainless steel), composite (e.g., carbon fiber PEEK composite) or polymer (e.g., polycarbonate), the distal end of which (distal to the wound when in use) functions as a handle and the proximal end of which (proximal to the wound when in use, with the tip adjacent to the bone) has a tip which is generally slightly curved. The tip is generally the narrowest part of the device and is designed to engage with the bone in use. While some retractor bars are narrow and have a relatively consistent width along their entire length (or slightly taper from the handle to the tip), many have a short portion of their blade that is wider than the retractor's blade in its handle section, sometimes much wider, forming a flange or wing. The flange or wing generally is co-planar with the rest of the blade at the same point along its length and generally is symmetrical about the longitudinal axis of the retractor bar. These wings are generally located towards the retractor bar's proximal end and serve to increase the area of the retractor bar which is in contact with the tissue being retracted. A retractor bar has a tissue-facing (rear-facing or posterior-facing) side and a side facing away from the tissue (front-facing or anterior-facing side), a handle end, and a tip or bone-interacting end. The tip is generally curved upwards towards the anterior-facing side (i.e., concave on that side). In use, the tip at the bone-interacting proximal end is placed against the bone between the bone and the tissue, and then a force is applied orthogonal to the distal handle end to displace the tissue. The longitudinal axis of a retractor bar is between the distal handle end and the proximal bone-interacting tip.

Since most surgeons or hospitals already own multiple variations of both self-retaining retractors and manual retractor bars, it would be desirable if self-retaining retractors could engage with retractor bars and replace the hands normally needed to hold the retractor bars in position during surgeries. Retractor bars generally have smooth surfaces so they are easy to clean and use. Self-retaining retractors are also often made from stainless steel. Even when the teeth of self-retaining retractor are pointed, they will tend slip along the smooth surface of the retractor bar when applying anything other than an orthogonal force.

U.S. Pat. No. 9,161,745 describes a retractor bar that has been modified, by introducing an opening into its planar blade, to enable a post on the arm of a self-retaining retractor to securely engage with the retractor bar. Because the posts of the self-retaining retractor extend radially outward from the retractor's opposing arms the retractor cannot be used to retract tissue alone, but only when used with one of several types of modular components. These modular components have openings through which one or more of the retractor's posts can extend to engage with the component, including the aforementioned modified retractor bar. Unfortunately, while the '745 retractor system (retractor and modular component) is self-retaining, it does not take advantage of the large number and variety of traditional retractor bar-type and self-retaining retractors already owned by hospitals and surgeons, and instead requires that an entire new set of custom retractor bars and self-retaining retractors and modular components be purchased.

There is, therefore, a need for a device that enables the self-retaining retractors of various designs already owned by surgeons and hospitals, such as Weitlaner and Gelpi retractors, to engage with manual retractor bars of various designs, such as Hohmann retractors, securely enough that the self-retaining retractor can replace the human hands currently needed to maintain tissue separation or displacement with manually operated retractor bars.

SUMMARY OF THE INVENTION

One aspect of the invention relates to an adaptor for use in a surgical retractor system including a surgical retractor bar having a longitudinal extent between a first end and a second end and a self-retaining retractor device with arms moveable between spaced and proximate positions. The adaptor includes a first plate coupled to a second plate, optionally by one or more connecting elements. A slot is formed between the first plate and the second plate and is configured to either longitudinally receive either the first end or the second end of the surgical retractor bar or laterally receive a lateral edge of the surgical retractor bar such that the adaptor is positioned along the longitudinal extent between the first end and the second end of the surgical retractor bar during use. One or more retaining elements are located on a first surface of the first plate opposite the slot between the first plate and the second plate. The one or more retaining elements are shaped to engage with at least a portion of the self-retaining retractor device to maintain the position of the self-retaining retractor device with respect to the first surface when a force is applied oblique to the first surface by the self-retaining retractor device.

Another aspect of the present invention relates to a kit including a first surgical retractor bar having a longitudinal extent between first and second ends and a self-retaining retractor device with arms moveable between spaced and proximate positions. The kit further includes a first adaptor of the present invention configured to be located along the longitudinal extent of the first surgical retractor bar and in contact with the self-retraining retractor device.

A further aspect of the present invention relates to a surgical retraction method using the kit of the present invention. The first adaptor is positioned along the longitudinal extent of the first surgical retractor bar. The first surgical retractor bar is positioned proximate to an incision or a wound to provide retraction of a tissue proximate to the incision or the wound. At least a portion the self-retaining retractor device is inserted into at least one of the one or more retaining elements on the first surface of the first plate. The inserting provides an oblique force against the first plate to maintain the position of the retractor bar against the tissue.

The present invention addresses advantageously provides an adaptor that enables certain self-retaining retractors to engage with certain manually operated retractors, thereby eliminating the need for an extra pair of hands holding the manually operated retractor bars in place during surgeries. In one embodiment, the adaptor is designed to "mate" a standard operating room retractor bar used for bone surgeries (e.g., Hohmann retractors) with those used for soft tissue (e.g., Weitlaner and Gelpi retractors) to allow the self-retaining soft-tissue retractor to hold the manual retractor bar or bars in position during a surgery.

In an embodiment, the present invention comprises an adaptor that can be attached to a retractor bar, or into which the retractor bar can be inserted (such as by slipping the adaptor over the tip or the handle of the retractor bar or onto the retractor bar from the side). In use, the adaptor is first positioned at an appropriate position along the retractor bar's longitudinal axis, and then the retractor bar with the adaptor attached is inserted into the surgical field. Generally when a retractor bar is inserted into a surgical field, such as an incision in a person's thigh exposing the femur, the tip, which often has a slight concave curvature, is placed adjacent to and in contact with the exposed bone, while the handle extends away from the bone and out of the surgical field. A second retractor bar with an adaptor attached thereto is optionally inserted into the surgical field with the tip adjacent to and in contact with the opposite side of the exposed bone.

In the case where there are two, facing retractor bars, each engaged with an adaptor of the present invention, the arms of the self-retaining retractor, or one or more teeth thereon, are operatively engaged with retaining elements on each of the two facing adaptors. Spreading the arms of the self-retaining retractor pushes the adaptors, and the retractor bars with which the adaptors are engaged, apart. If only one retractor bar is being used, one arm of the self-retaining retractor is engaged with the adaptor attached to that retractor bar and the other arm is engaged directly with tissue, and the two are pushed apart by spreading the arms of the self-retaining retractor. As the arms of the self-retaining retractor push the retractor bars apart (or the single retractor bar and the tissue) to open up the surgical field, the angle of the retractor bar and adaptor relative to the perpendicular (directly out of the surgical field) becomes more and more oblique. As a result, while the angle of the force applied by the self-retaining retractor to the adaptor may begin roughly orthogonal to the adaptor's anterior plate and the retractor bar, the angle becomes more and more oblique as the arms of the self-retaining retractor push the adaptors and retractor bars apart. This is because the retractor bars are generally anchored at their tip against a bone and so the handle end of the retractor bar in effect rotates around the anchored tip as it is pushed outwards by the self-retaining retractor's arms.

DETAILED DESCRIPTION

Although claimed subject matter will be described in terms of certain embodiments and examples, other embodiments and examples, including embodiments and examples that do not provide all of the benefits and features set forth herein, are also within the scope of this disclosure. Various structural changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

One aspect of the invention relates to an adaptor for use in a surgical retractor system including a surgical retractor bar having a longitudinal extent between a first end and a second end and a self-retaining retractor device with arms moveable between spaced and proximate positions. The adaptor includes a first plate coupled to a second plate, optionally by one or more connecting elements. A slot is formed between the first plate and the second plate and is configured to either longitudinally receive either the first end or the second end of the surgical retractor bar or laterally receive a lateral edge of the surgical retractor bar such that the adaptor is positioned along the longitudinal extent between the first end and the second end of the surgical retractor bar during use. One or more retaining elements are located on a first surface of the first plate opposite the slot between the first plate and the second plate. The one or more retaining elements are shaped to engage with at least a portion of the self-retaining retractor device to maintain the position of the self-retaining retractor device with respect to the first surface when a force is applied oblique to the first surface by the self-retaining retractor device.

An exemplary adaptor 100 is illustrated in FIGS. 2-5. The adaptor 100 comprises an anterior plate 110 and a posterior plate 112 which are roughly parallel to each other. The anterior plate 110 and the posterior plate 112 are attached to one another, optionally by one or more connecting elements 114. A slot 102 (e.g., recess, lumen) is formed between the anterior plate 110 and the posterior plate 112 into which a retractor bar can be inserted. The adaptor 100 has an orientation when properly used, with a proximal end 122 and a distal end 120. The distal end 120 is further away from deepest part of the surgical incision (i.e., oriented closer to the handle end of the retractor bar when in use) and the proximal end is closer to the deepest part of the surgical incision (i.e., oriented closer to the tip end of the retractor bar which may be engaged with the bone). The longitudinal axis of the adaptor is between its distal and proximal ends and should be substantially parallel to the longitudinal axis of the retractor bar it is attached to when in use.

The front or anterior plate 110 is positioned away from the tissue when engaged with the retractor bar (i.e., the retractor bar and the posterior plate 112 are between the anterior plate 110 and the tissue being displaced). The anterior plate 110 has an inward-facing surface 132 (i.e., facing the retractor bar and the posterior plate 112) and an outward-facing surface 130 (facing away from the retractor bar and away from the posterior plate 112). The outward-facing surface 130 comprises one or more retaining elements 124, such as recesses or projections, adapted to positively engage with at least one tooth or post of a self-retaining retractor and prevent the tooth from slipping along the outward-facing surface 130 of the adaptor 100 when a force is applied obliquely. In particular, the retaining elements 124 are designed to keep the tooth or post from slipping along the outward-facing surface 130 towards the distal end 120 of the adaptor 100 as the angle of the retractor bar and the adaptor 100 increases with their displacement.

In use, the inward-facing surface 132 of the anterior plate 110 of the adaptor 100 is located adjacent to and against the front-facing side of the retractor bar. The anterior plate 110 may be smooth or rough on its inward-facing surface 132. The inward-facing surface 132 optionally has a layer 134 of material on it (e.g., magnetic material, foam, ceramic, metal, adhesive, polymer, rubber, felt, fabric) that optionally forms a protective layer between the anterior plate 110 and the retractor bar's anterior-facing surface (shown in FIG. 2 only) and/or increases the friction between the anterior plate 110 and the retractor bar to help prevent the adaptor 100 from sliding relative to the retractor bar.

The posterior plate 112 has an inward-facing surface 126 (i.e., oriented towards and against the retractor bar's posterior-facing side when in use and also towards the anterior plate 110) and an outward-facing surface 128 (i.e., oriented towards and against the tissue being displaced when in use and away from the anterior plate 110). In use, the posterior plate 112 is positioned between the retractor bar and the tissue being displaced. The posterior plate 112 may be smooth or rough on its inward-facing surface 126. The inward-facing surface 126 may have an optional layer 136 of material on it (e.g., magnetic material, foam, ceramic, metal, adhesive, polymer, rubber, felt, fabric) that optionally forms a protective layer between the posterior plate 112 and the retractor bar (shown in FIG. 2 only) and/or helps prevent the adaptor 100 from sliding along the longitudinal axis of the retractor bar when in use by increasing the friction between the adaptor 100 and the retractor bar. The outward-facing surface 128 is optionally roughened with roughing elements 138, such as with corrugations, indentations, bosses, studs, spikes, grooves, ridges, rough coating (e.g., sand-type epoxy or paint), by blasting with sand or ball bearings, etched lines or grid, or by other means. Such roughening is intended to resist movement of the posterior plate 112 relative to the tissue when a force is applied to the adaptor 100. In the examples shown in FIGS. 2, 3, and 4, the roughening elements 138 are small conical bosses (protrusions) protruding outwards from the outward-facing surface 128 of the posterior plate 112. The posterior plate 112 and the anterior plate 110 may have a curvature. This curvature may match that of the retractor bars with which the adaptor 100 is intended to be used.

The inward-facing surface 132 of the anterior plate 110 and the inward-facing surface 126 of the posterior plate 112 are roughly parallel, or if curved, roughly concentric, such that the spacing between them is consistent. In an embodiment, the posterior plate 112 and the anterior plate 110 have a curvature conforming to that of the retractor bars with which the adaptor 100 is intended to be used.

The anterior plate 110 is attached to the posterior plate 112, either directly or via one or more optional connecting elements 114 connected to both the anterior plate 110 and the posterior plate 112. In embodiments where there are no connecting elements, the anterior plate 110 and the posterior plate 112 are attached directly to each other, such as by a weld or adhesive, and are shaped to form the slot 102 with cross-sectional dimensions sufficient to permit at least a portion of a retractor bar to be disposed within the slot 102. The embodiment shown in FIG. 7 comprises a curved anterior plate 110 and a curved posterior plate 112 that are joined directly at seams 146. In this embodiment, because the concave side of the anterior plate 110 (i.e., its inward-facing surface is concave) is facing the concave side of the posterior plate 112 (i.e., its inward-facing surface is concave), slot 102 is formed between them. In an embodiment, the adaptor 100 is formed from a single piece of material, such as by an injection molding, extrusion, 3D printing, or casting, and the slot 102 is formed between the posterior plate 112 portion of the adaptor 100 and the anterior plate 110 portion of the adaptor 100. In an embodiment, the posterior plate 112 and/or the anterior plate 110 incorporates a portion that is angled (e.g., orthogonal) relative to the main body of the plate (i.e., the portion over the face of the retractor bar blade when disposed within the slot 102). This angled portion is then attached to the other plate, thereby connecting the anterior plate 110 and the posterior plate 112 and creating the slot 102. Each bent portion can run the entire length of the plate or just along portion, and can include two or more separated angled sections.

In embodiments comprising the one or more connection elements 114 joining the posterior plate 112 and the anterior plate 110, the connecting elements 114 may be planar or non-planar or any other appropriate shape. The connecting elements 114 are fixedly attached to both the anterior plate 110 and the posterior plate 112. The connecting elements 114 function to: create a separation between the anterior plate 110 and the posterior plate 112 (i.e., create the slot 102); limit lateral movement of the anterior plate 110 and the posterior plate 112 relative to each other; prevent separation of the anterior plate 110 and the posterior plate 112 under pressure; and/or transfer any force applied to one plate to the other plate, without substantial deformation (or any). In the embodiment shown in FIGS. 2-5, each of the connecting elements 114 is a separate rectangular plate attached along one edge to one lateral edge of the anterior plate 110 and along its opposite edge to one lateral edge of the posterior plate 112 (in an embodiment, the connecting element 114 is an integral part of the anterior plate 110 or the posterior plate 112 and comprises a narrow, rectangular section thereof that is bent orthogonal to the plate and then attached to the other plate). The connecting elements 114 may also function as a spring clamp that pulls the anterior plate 110 and the posterior plate 112 toward the retractor bar, holding it in place between them, but allowing the adaptor 100 to slide relative to the retractor bar under a moderate force, such as in the embodiment shown in FIGS. 10A and 10B. The connecting elements 114 may be removable or adjustable, such as in an adaptor where fasteners are used to attach the anterior plate 110 and the posterior plate 112 to each other. In one embodiment, the connecting elements 114 are attached to the distal end of each of the anterior plate 110 and the posterior plate 112, and has a rectangular opening in it of sufficient width and height for the handle or tip end of certain retractor bars to pass through.

The slot 102 is formed between the anterior plate 110 and the posterior plate 112 of the adaptor 100, which are separated by a sufficient distance that retractor bars having a certain thickness can fit in between. The slot 102 can be closed on all sides but the two ends, or be open on one side and the two ends. The slot 102 is formed such that a retractor bar (such as those of an appropriate size or size range) can pass through the adaptor 100 along its longitudinal axis (from the distal end 120 to the proximal end 122 or vice versa) or be inserted from the side. In some embodiments, the anterior plate 110 and the posterior plate 112 are connected to form slot 102 that is a lumen aligned with the longitudinal axis of the adaptor 100. Retractor bars generally have a rectangular cross-section orthogonal to its longitudinal axis, and the slot 102 is generally slightly larger than the largest cross section of the retractor bar in order that the adaptor 100 can pass over the retractor bar when being moved into position (the exception is if the anterior plate 110 and the posterior plate 112 of the adaptor 100 or connecting elements 114 are flexible so that the slot 102 can enlarge under pressure of a retractor bar being inserted therein).

In some embodiments, the adaptor 100 will be slipped over the handle of the retractor bar and slid down into position. In some embodiments, the adaptor 100 will be slipped over the proximal tip end of the retractor bar and slid up into position. It is desirable that the adaptor 100 be able to slide relative to the retractor bar without excessive force so that it can readily be moved into position, although some resistance to movement may be desirable to help keep the adaptor 100 stationary relative to the retractor bar once it has been positioned thereon. In some embodiments, the slot 102 is a lumen into which a retractor bar can be inserted, where the lumen has a low-aspect ratio cross-section (e.g., a rectangular, elliptical, oval shape with a low short sides to long sides or minor axis to major axis ratio) to accept and retain the retractor bar (e.g., retractor bar with a thin but wide cross-section) in a desired orientation relative to the adaptor 100 in order that it not shift excessively laterally relative to the bar or rotate around the bar.

In the embodiment shown in FIGS. 2-5, the anterior plate 110 is suspended over the posterior plate by two connecting elements 114, one on each side of the anterior plate 110. The connecting elements 114, together with the anterior plate 110 and the posterior plate 112, form the slot 102 (lumen, channel) aligned with the longitudinal axis of the adaptor 100 with one open end facing the distal end 120 of the adaptor 100 and the other open end facing its proximal end 122. In the embodiment shown in FIG. 6A, the slot 102 (not shown) is formed by the pair of narrow connecting elements 114 on either side of the anterior plate 110 proximate the proximal end 122 of the adaptor 100 that connect to the posterior plate 110 towards the proximal end 122, while in the embodiment shown in FIG. 6B, the slot 102 (not shown) is formed by the pair of narrow connecting elements 114 on either side of the anterior plate 110 proximate the distal end 120 of the adaptor 100 that connect to the posterior plate 112 toward the distal end 122. The connecting elements 114 suspend and cantilever the anterior plate 110 over the posterior plate 112. In use, applying a force with a self-retaining retractor to the retaining element 124 on the anterior plate 110 presses it towards the retractor bar disposed within the slot 102 (not shown). That pressure and the force transferred from the anterior plate 110 through the connecting elements 114 and the retractor bar transmit a force to the posterior plate 112 and thence to the tissue.

Figure 6A:
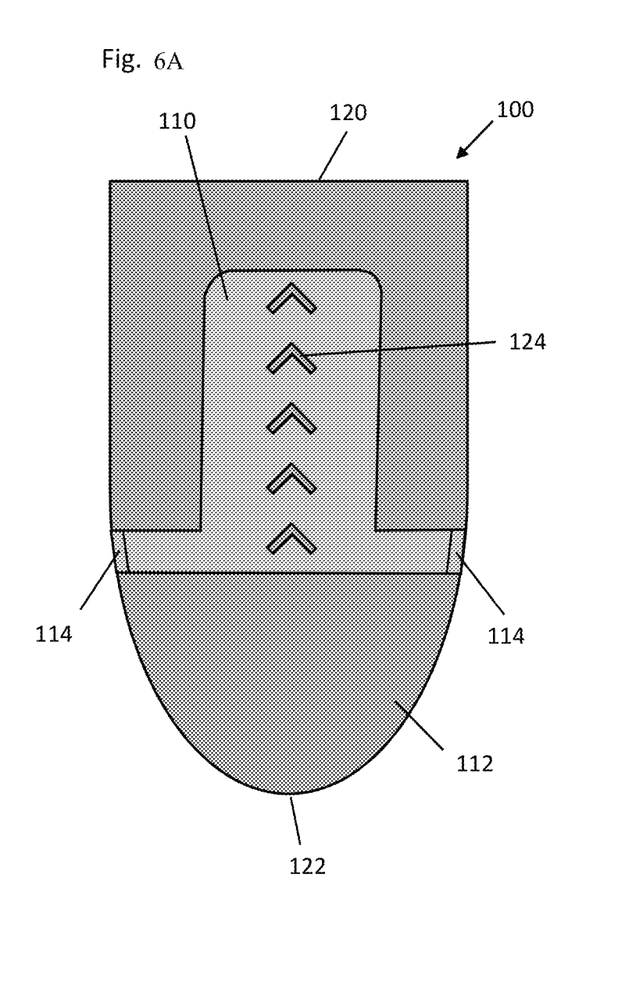
FIGS. 6A and 6B are a front view and a rear view, respectively, of another exemplary adaptor, for use with surgical retractors, of the present invention.
Figure 6B:
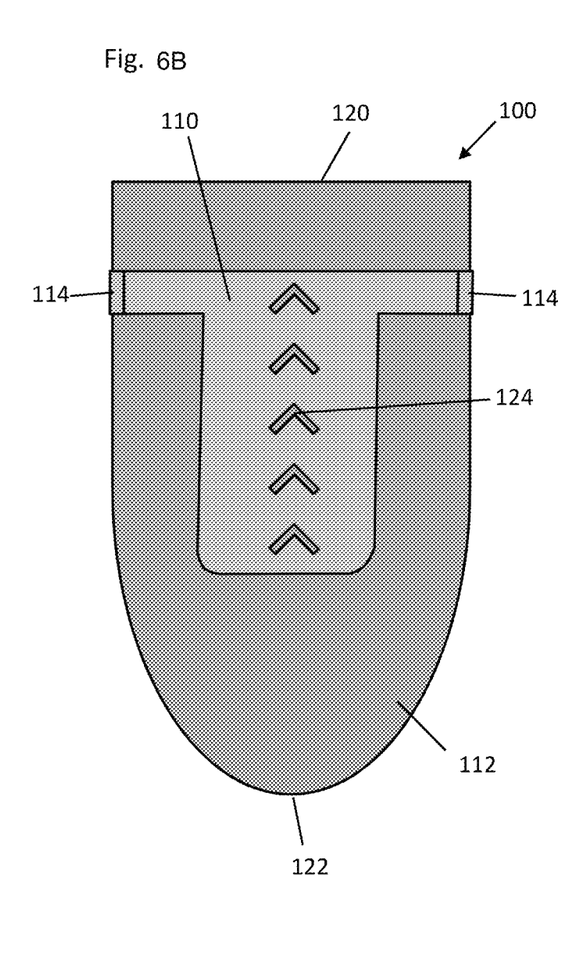

The design of the adaptor 100 shown in FIG. 6B enables it to be used with a retractor bar having a section (e.g., a flange) near its proximal end that is wider than the slot 102 itself (i.e., the distance between the inner surfaces of the two connecting elements 114 flanking the slot 102)—the portion of the anterior plate 110 to the proximal side of the connecting elements 114 is able to slip over the outward facing surface of that wider section of the retractor bar, not being bounded laterally at that point by any connecting element between it and the posterior plate 112. If the adaptor 100 was slipped over the distal end of the retractor and slid down the handle towards the tip, the connecting elements 114 forming the slot 102 (not shown) will eventually reach the distal end of the wide section and, the slot 102 (not shown) formed being narrower than the wide flange section, will stop against it.

The slot 102 may be sized or formed such that the force applied by the self-retaining retractor to the anterior plate 110 will be transferred to the posterior plate 112: (a) through direct contact (i.e., both the anterior plate 110 and the posterior plate 112 are in contact with the retractor bar in the slot 102; (b) via the connection elements 114; or (c) by a combination thereof. In all cases, the retractor bar and the adaptor 100 may be able to move relative to each other so that as the jaws of the self-retaining retractor spread and the angle of the retractor bar increases, the position of the adaptor 100 relative to the proximal and distal ends of the retractor bar may change.

Figure 5:
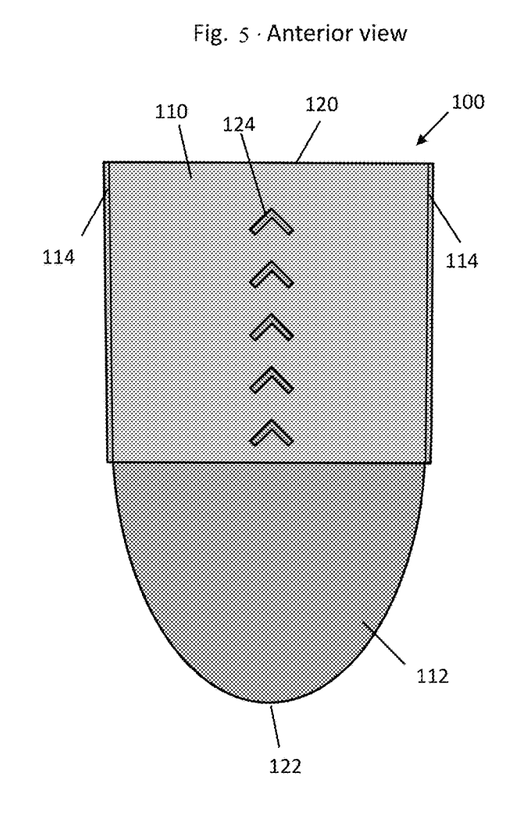
FIG. 5 is a front view of the exemplary adaptor shown in FIG. 1.

In use, one or more teeth (or posts) of the self-retaining retractor will be exerting a force oblique to the outward-facing side 130 of the anterior plate 110. Absent some means of securely engaging the one or more teeth with the anterior plate 110 or a very high coefficient of friction between the tooth and the anterior plate 110, the one or more teeth will eventually slip, which is undesirable. The adaptor 100 of the present invention therefore incorporates one or more retaining elements 124 on the outward-facing side 130 of the anterior plate 110 that enable one or more of the teeth of a standard self-retaining retractor to securely engage with the adaptor 100 and prevent any slippage of the one or more teeth relative to the adaptor 100 once a force is applied by the self-retaining retractor, even as the angle of the adaptor and retraction bar to the perpendicular grows. An appropriate retaining element 124 is any structure that will prevent slippage of the tooth or teeth of the self-retaining retractor relative to the anterior plate 110 of the adaptor 100, even at an angle of 35, 45, 60 degrees or more. The retaining element(s) 124 enable secure engagement with one or more teeth of various self-retaining retractors, the angle, tip, and orientation of which vary considerably. Appropriate retaining elements 124 include but are not limited to an indentation, hole, ridge, groove, inverted-V-shaped ridge (as shown in FIG. 5) or inverted-V-shaped groove (vertex of V pointing towards the distal end 120 of the adaptor 100), flange, cross-hatched grooves, lip, concave flange, roughened area, and deformable polymer element. There may be multiple retaining elements 124, arranged on the outward-facing surface 130 of the anterior plate 110 so as to provide a user with a choice of locations at which to engage the self-retaining retractor with the adaptor 100, such as aligned along the longitudinal axis of the adaptor 100 and/or orthogonal to the longitudinal axis. The retaining elements 124 may be designed to be narrow enough laterally so that it engages with a single tooth without interfering with adjacent teeth. The positioning of the retaining elements 124, such as over the longitudinal central axis of the anterior plate 110 may minimize the probability that an oblique force applied to the retaining elements 124 will create a rotational force on the anterior plate 110.

In use, the force exerted by the self-retaining retractor on the anterior plate 110 of the adaptor 100 is transferred to the posterior plate 112, which will result in a force being applied to the displaced tissue. The retaining elements 124 on the anterior plate 110 prevent movement of the self-retaining retractor's teeth relative to the adaptor 100, even as the angle between them becomes more oblique under force. The connections between the posterior plate 112 and the anterior plate 110, such as by optional connecting element(s) 114, prevent the anterior plate 110 to which the force is applied from moving substantially relative to the posterior plate 112. A layer of high friction material 134 on the inward-facing side 132 of the anterior plate 110 may help resist movement of the anterior plate 110 relative to the retractor bar, although some movement may be desirable. Transfer of force from the anterior plate 110 to the posterior plate 112 is direct, when the two are directly connected, via the connecting element(s) 114 when they are present, or via the retractor bar (such as if the connecting elements 114 are not rigid), or a combination of thereof. Force is transferred from the anterior plate 110 to the retractor bar via direct contact. Force is transferred to the tissue being displaced by both the posterior plate 112 and the portion of the retractor bar that is in direct contact with the tissue. The engagement-enhancing features 138 on the outward-facing surface 126 of the posterior plate 112 help prevent movement of the posterior plate 112 relative to the tissue. In some circumstances, in order for the position of the posterior plate 112 relative to the tissue to remain constant, the adaptor 100 may slide along retractor bar toward its handle end slightly as the tissue separation is increasing. In some circumstances, the position of the adaptor 100 relative to the retractor bar may remain constant and there may be slippage between the tissue and the outward-facing surface 128 of the posterior plate 112.

The dimensions of adaptor 100 and its various elements can be varied so that a particular adaptor 100 of the present invention works with retractor bars within a specific range of sizes and/or having a particular design and with self-retaining retractors of a certain size and/or design. The adaptor 100 is preferably formed of a relatively rigid material for strength and stability, such as a metal (e.g., stainless steel), composite (e.g., Kevlar®) or plastic (e.g., polycarbonate, PVC), which is robust enough that the force of the self-retaining retractor or tissue on the adaptor 100 will not cause substantial deformation of or damage to the adaptor 100 (i.e., failure of the adaptor 100 or any element thereof), and that is capable of transferring the force of the self-retaining retractor from the anterior plate 110 to the posterior plate 112. A relatively rigid material capable of deforming or flexing slightly and springing back to its original position or form (e.g., spring steel) may be useful in certain embodiments.

The anterior plate 110 and the posterior plate 112 may have any suitable size. In some cases it may be desirable that their width (i.e., the dimension orthogonal to its longitudinal axis between the center of its distal and proximal ends) be only slightly greater than that of the retractor bars they will be used with so as not to obstruct the view of the surgical field (e.g., if the retractor bar is 4 cm at its widest, the inner width of the slot 102 need only be slightly greater than 4 cm, and the adaptor 102 need only be enough wider to account for any material forming the slot 102). In other cases, it may be desirable for at least the posterior plate 112 to be substantially wider than the retractor bar it is being used with to spread pressure on the tissue over a greater area. In general, the anterior 110 plate need only be wide enough at its widest point to form the slot 102 to allow the retractor bar to be inserted and wide enough at its narrowest point to provide sufficient space for the retaining element or elements 124 wherever they are integrated into the anterior plate 110.

The adaptor 110 can be sized for use with any retractor bar in use currently or which may be in use in the future, from the smallest to the largest.

The corners of the anterior plate 110 and the posterior plate 112 may be rounded to help reduce the chance they will catch on tissue, gloves, scrubs, etc. The proximal end of the posterior plate 112 may be rounded (e.g., bullet or surf board shaped) so that it is easier to adjust its position once it has been engaged with a retractor bar and the retractor has been positioned in the surgical incision. The edges of all elements of the adaptor 100 are preferably smooth and rounded.

In an embodiment, the adaptor 100 has a light source and battery power source for the light source attached to or incorporated into the anterior plate 110 or the posterior plate 112. The light is preferably oriented towards the proximal end 122 of the adaptor 100 so that it will illuminate the surgical field when in position on a retractor bar. The light may have shades and/or reflectors that direct illumination into the surgical field and/or away from the surgeon's eyes. The light is preferably an LED. In an embodiment, the anterior plate 110 comprises a clip or mount for attaching a light source, such as an optical fiber, or other useful items.

Figure 7:
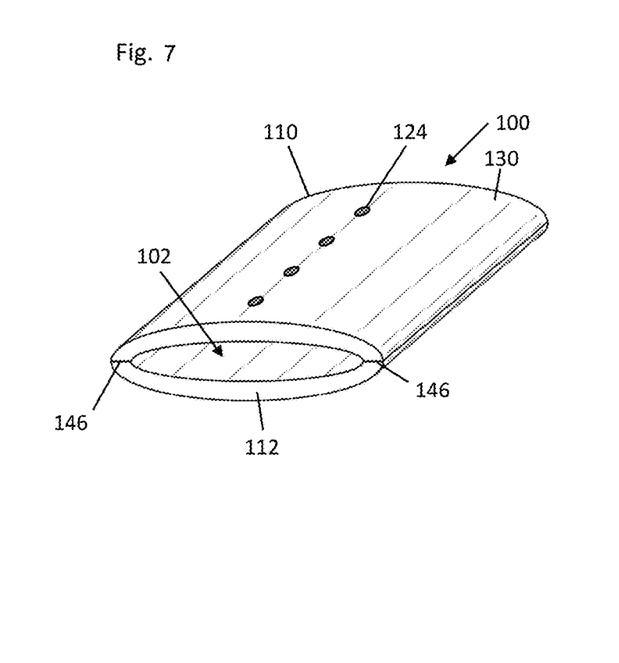
FIG. 7 is a perspective view of another exemplary adaptor, for use with surgical retractors, of the present invention.

In an embodiment shown in FIG. 7, the adaptor 100 comprises anterior plate 110 and posterior plate 112 that are connected to each other at a seam 146 (in a manner of speaking, a weld or adhesive connection can functionally be considered a connecting element). In this embodiment, the anterior plate 110 and the posterior plate 112 are concave cylinder segments that, when joined along their edges with their concave side facing towards each other, form the slot 102 into which a retractor bar can be inserted (either the posterior plate 112 or the anterior plate 110 can be planar in other embodiments, as long as the concavity of the other plate is sufficient to form the slot 102 with appropriate dimensions). The adaptor 100 further comprises multiple retaining elements 124 that are indentations or holes axially aligned on the outward-facing side 130 of the anterior plate 110 (i.e., the side opposite the slot 102). The retaining elements 124 are centered laterally. The rear-facing side of the posterior plate (not shown) incorporates roughening elements 138, such as roughness, protrusions, grooves, or ridges. In an embodiment, the seam 146 only extends partway from the distal end 120 of the adaptor 100 towards the proximal end 122, and there is an opening between the posterior plate 112 and the anterior plate 110 that is sufficient to accommodate the wide flanges of a retractor bar (this embodiment will operate similarly to the embodiment shown in FIG. 6B).

Figure 8:
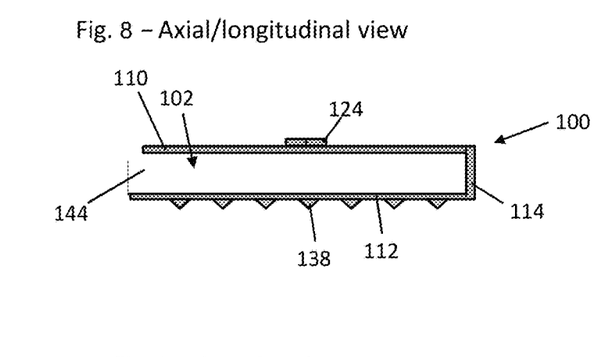
FIG. 8 is a top view of another exemplary adaptor, for use with surgical retractors, of the present invention.
Figure 9:
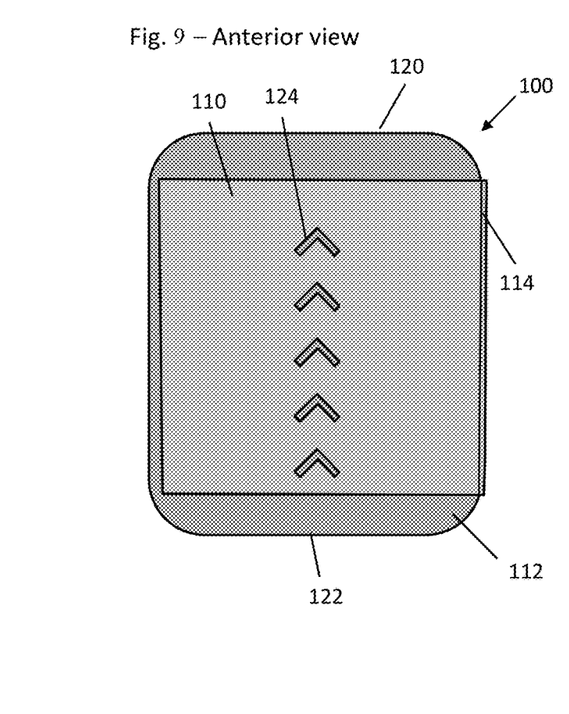
FIG. 9 is a rear view of the exemplary adaptor shown in FIG. 8.
Figure 10A:
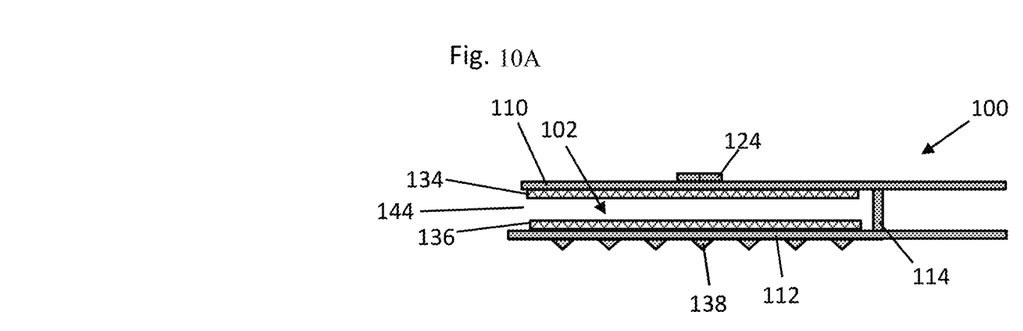
FIGS. 10A and 10B are top view of another exemplary adaptor, for use with surgical retractors, of the present invention in a closed and open position, respectively.
Figure 10B:
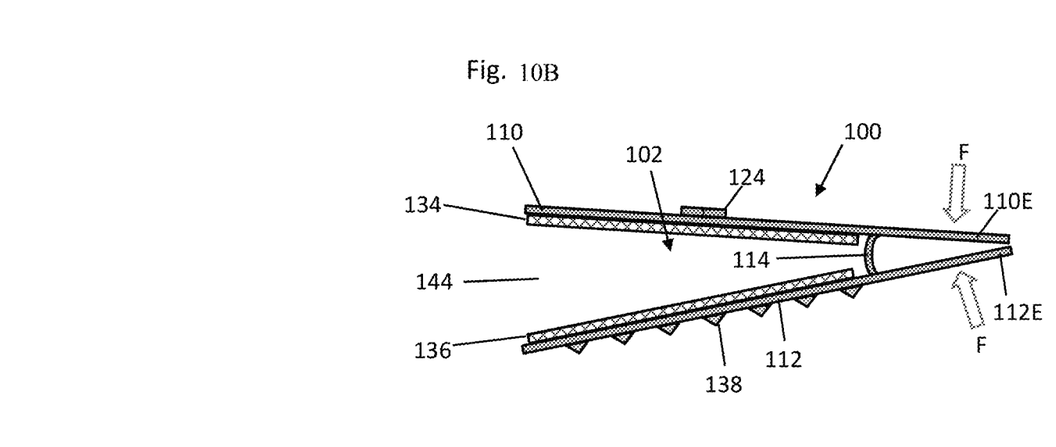

In some embodiments, such as shown in FIGS. 8 and 9, the anterior plate 110 and the posterior plate 112 are joined by connecting element 114 on one lateral side of the slot 102 only, leaving the other lateral side 144 of the slot 102 open. In such embodiments, the retractor bar can be slipped into the slot 102 laterally as well as through the proximal or distal end of the slot 102. In some embodiments where there is an open lateral side 144 of the slot 102, such as shown in FIGS. 10A and 10B, the connecting element 114 incorporates a spring element (such as a spring hinge), or is made of a spring-like material (e.g., spring steel or polymer that will deform/flex under certain levels of force but will return to its original shape once the force is removed), and the anterior plate 110 and the posterior plate 112 extend beyond the connecting element 114 external to the slot 102, such that the connecting element 114 will act as a fulcrum when the extended portion 110E of the anterior plate 110 and the extended portion 112E of the posterior plate 112 are pressed toward each other. There is optionally a layer 134 of material on the side of the anterior plate 110 and/or the side of the posterior plate 112 facing into the slot 102. Simultaneously squeezing together (applying a force F) to the extended portions 110E and 112E of the anterior 110 and the posterior plate 112, respectively, flexes/deforms the spring connecting element 114 and separates the other portion of the anterior plate 110 and the posterior plate 112, increasing the size of the lateral opening 144 of the slot 102. The adaptor 100 can then be slipped laterally onto a retractor bar (e.g., clipped on); when the pressure on the extended portions 110E and 112E is released, the anterior plate 110 and posterior plate 112 will spring back to their original position, squeezing the retractor bar between them. In this embodiment, a force applied to the retaining element 124 on the anterior plate 110 may push it towards the retractor bar in the slot 102 and then push it towards the posterior plate 112, or at least at their ends proximal to the lateral opening 144.

Another aspect of the present invention relates to a kit including a first surgical retractor bar having a longitudinal extent between first and second ends and a self-retaining retractor device with arms moveable between spaced and proximate positions. The kit further includes a first adaptor of the present invention configured to be located along the longitudinal extent of the first surgical retractor bar and in contact with the self-retraining retractor device.

A further aspect of the present invention relates to a surgical retraction method using the kit of the present invention. The first adaptor is positioned along the longitudinal extent of the first surgical retractor bar. The first surgical retractor bar is positioned proximate to an incision or a wound to provide retraction of a tissue proximate to the incision or the wound. At least a portion the self-retaining retractor device is inserted into at least one of the one or more retaining elements on the first surface of the first plate. The inserting provides an oblique force against the first plate to maintain the position of the retractor bar against the tissue.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An adaptor for use in a surgical retractor system including a surgical retractor bar having a longitudinal extent between a first end and a second end, and a self-retaining retractor device with arms moveable between spaced and proximate positions, the adaptor comprising:
   a first plate;
   a second plate coupled to the first plate, the second plate spaced apart from the first plate;
   a slot formed between and at least partially defined by the first plate and the second plate, the slot receiving the surgical retractor bar such that the first plate and the second plate are positioned along the longitudinal extent between the first end and the second end of the surgical retractor bar during use; and
   a plurality of retaining elements located on an outward surface of the first plate, the outward surface positioned opposite the slot formed between the first plate and the second plate,
   wherein the plurality of retaining elements engaging with at least a portion of the self-retaining retractor device to maintain the position of the self-retaining retractor device with respect to the outward surface when a force is applied oblique to the outward surface by the self-retaining retractor device.

2. The adaptor of claim 1, wherein the first plate and the second plate are substantially parallel to one another.

3. The adaptor of claim 1, wherein the slot is configured such that a longitudinal extent of the adaptor between a distal end and a proximal end is substantially parallel to the longitudinal extent of the surgical retractor bar when the at least a portion of the surgical retractor bar is positioned within the adaptor.

4. The adaptor of claim 1, wherein the retaining elements are recesses formed in or projections extending from the outward surface.

5. The adaptor of claim 1, wherein the retaining elements are one or more of inverted v-shaped ridges or grooves, flanges, roughened areas, cross-hatched grooves, lips, ridges, grooves, concave flanges, or deformable elements.

6. The adaptor of claim 1, wherein at least one inward surface of the first plate or the second plate located within the slot between the first plate and the second plate comprises a layer of material to contact the surgical retractor bar when inserted in the slot.

7. The adaptor of claim 6, wherein the layer of material comprises an adhesive, a ceramic, a foam, a metal, a rubber, a polymer, a felt, or a fabric, or any combination thereof.

8. The adaptor of claim 1, wherein the second plate has an outward surface located opposite the slot, the outward surface contacting a tissue and resisting movement of the second plate with respect to the tissue during use.

9. The adaptor of claim 8, wherein the outward surface of the second plate has one or more of corrugations, indentations, bosses, studs, spikes, grooves ridges, a coating, or etchings in the outward surface.

10. The adaptor of claim 1, further including a first connecting element coupling the first plate to the second plate, the first connecting element extending at least partially between a proximal end and a distal end of the first plate and the second plate, respectively.

11. The adaptor of claim 10, wherein the first connecting element is configured to make size adjustments to the slot between the first plate and the second plate.

12. The adaptor of claim 10, wherein the first connecting element is coupled to the first plate and the second plate adjacent a first side of the first plate and the second plate.

13. The adaptor of claim 12, further including a second connecting element coupling the first plate to the second plate, the second connecting element extending at least partially between the proximal end and the distal end of the first plate and the second plate, respectively, opposite the first connecting element,
wherein the slot is a lumen.

14. The adaptor of claim 10, wherein the first connecting element is coupled to the first plate and the second plate between a first side of the first plate and the second plate, and a second side of the first plate and the second plate,
wherein the first connecting element is configured to function as a spring-clamp between the first plate and the second plate.

15. The adaptor of claim 1, wherein the plurality of retaining elements are centrally located on the outward surface of the first plate.

16. The adaptor of claim 1, wherein the plurality of retaining elements are centered laterally over the second plate along the longitudinal extent of the first plate.

17. The adaptor of claim 1 further comprising: a light source attached to or located within the first plate.

18. The adaptor of claim 17, wherein the light source is positioned near the proximal end of the adaptor.

19. A kit comprising:
a self-retaining retractor device with arms moveable between spaced and proximate positions;
a first adaptor receiving a longitudinal extent of a first surgical retractor bar and in contact with the self-retraining retractor device, the first adaptor including:
at least one first connecting element,
a first plate coupled directly to the at least one first connecting element,
a second plate coupled directly to the at least one first connecting element, the second plate coupled to the first plate via the at least one first connecting element and spaced apart from the first plate,
a first slot formed between and at least partially defined by the first plate, the second plate, and the at least one first connecting element, respectively, the first slot receiving the first surgical retractor bar,
one or more retaining elements located on an outward surface of the first plate, the outward surface of the first plate opposite the first slot,
wherein the one or more retaining elements engage with at least a portion of the self-retaining retractor device to maintain the position of the self-retaining retractor device with respect to the outward surface when a force is applied oblique to the outward surface of the first plate by the self-retaining retractor device; and
a plurality of roughening elements positioned on an outward surface of the second plate, the outward surface of the second plate opposite the first slot formed between the first plate and the second plate; and a second adaptor receiving a longitudinal extent of a second surgical retractor bar and in contact with the self-retraining retractor device, the first adaptor including:
at least one second connecting element,
a third plate coupled directly to the at least one second connecting element,
a fourth plate coupled directly to the at least one second connecting element,
the fourth plate coupled to the third plate via the at least one second connecting element and spaced apart from the third plate,
a second slot formed between and at least partially defined by the third plate, the fourth plate, and the at least one second connecting element, respectively, the second slot receiving the second surgical retractor bar,
one or more retaining elements located on an outward surface of the third plate, the outward surface of the third plate opposite the second slot,
wherein the one or more retaining elements engage with at least a portion of the self-retaining retractor device to maintain the position of the self-retaining retractor device with respect to the outward surface when a force is applied oblique to the outward surface of the third plate by the self-retaining retractor device; and
a plurality of roughening elements positioned on an outward surface of the fourth plate, the outward surface of the fourth plate opposite the second slot formed between the third plate and the fourth plate.

20. An adaptor for use in a surgical retractor system including a surgical retractor bar having a longitudinal extent between a first end and a second end, and a self-retaining retractor device with arms moveable between spaced and proximate positions, the adaptor comprising:
a first plate including:
an outward surface,
one or more retaining elements located on the outward surface of the first plate,
an inward surface positioned opposite the outward surface, and
a first material layer disposed over at least a portion of the inward surface of the first plate;
a second plate coupled to the first plate, the second plate spaced apart from the first plate and including:
an outward surface,
an inward surface positioned opposite the outward surface, and
a second material layer disposed over at least a portion of the inward surface of the second plate; and
a slot formed between and at least partially defined by the first material layer of the first plate and the second material layer of the second plate, the slot receiving the surgical retractor bar such that the first material layer of the first plate and the second material layer of the second plate are positioned along the longitudinal extent between the first end and the second end of the surgical retractor bar,
wherein the one or more retaining elements engaging with at least a portion of the self-retaining retractor device to maintain the position of the self-retaining retractor device with respect to the outward surface of the first plate when a force is applied oblique to the outward surface of the first plate by the self-retaining retractor device.

* * * * *